(12) United States Patent
Wessling et al.

(10) Patent No.: US 7,977,487 B2
(45) Date of Patent: Jul. 12, 2011

(54) METHOD FOR PRODUCING N,N-BIS (PYRIDIN- 2YLMETHYL)-1,1-BIS(PYRIDIN-2-YL)-1-AMINOALKANE COMPOUNDS AND METAL COMPLEX SALTS CONTAINING THESE COMPOUNDS

(75) Inventors: Michael Wessling, Kandern (DE); Barbara Duecker, Mainz (DE); Nicole Nitschke, Eschborn (DE)

(73) Assignee: Clariant Produkte (Deutschland) GmbH, Frankfurt am Main (DE)

( * ) Notice: Subject to any disclaimer, the term of this patent is extended or adjusted under 35 U.S.C. 154(b) by 443 days.

(21) Appl. No.: 11/921,551

(22) PCT Filed: May 26, 2006

(86) PCT No.: PCT/EP2006/005023
§ 371 (c)(1), (2), (4) Date: Feb. 25, 2009

(87) PCT Pub. No.: WO2006/128635
PCT Pub. Date: Dec. 7, 2006

(65) Prior Publication Data
US 2009/0221831 A1  Sep. 3, 2009

(30) Foreign Application Priority Data
Jun. 1, 2005  (DE) .......................... 10 2005 024 997

(51) Int. Cl.
C07D 401/14 (2006.01)
C07F 15/02 (2006.01)

(52) U.S. Cl. ........................................... 546/264; 546/2
(58) Field of Classification Search ............... 546/2, 264
See application file for complete search history.

(56) References Cited

FOREIGN PATENT DOCUMENTS
EP  0909809 A2  4/1999

OTHER PUBLICATIONS
International Search Report of corresponding Application No. PCT/EP2006/005023, mailed Nov. 15, 2006.

*Primary Examiner* — Patricia L Morris
(74) *Attorney, Agent, or Firm* — Tod A. Waldrop

(57) ABSTRACT

The invention relates to a method for producing the compositions cited in the title. According to this method: dipyridyl ketone is reacted with hydroxylamine; the oxime obtained thereby is reduced without intermediate isolation to form 1,1-di-(2-pyridyl)-methylamine, and; this amine is firstly reacted with 1 to 1.5 molar equivalent of picolyl chloride and then with another 1 to 1.5 molar equivalent of picolyl chloride to form the amine of formula (1).

(1)

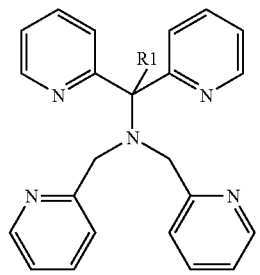

This amine is purified via the tetrafluoroborate salt and subsequently alkylated with an alkyl iodide. This method represents an improvement with regard to prior art methods for producing these compounds.

3 Claims, No Drawings

METHOD FOR PRODUCING N,N-BIS (PYRIDIN-2YLMETHYL)-1,1-BIS(PYRIDIN-2-YL)-1-AMINOALKANE COMPOUNDS AND METAL COMPLEX SALTS CONTAINING THESE COMPOUNDS

N,N-Bis(pyridin-2-yl-methyl)-1,1-bis(pyridin-2-yl)-1-aminoalkane compounds and a process for preparing them are known from EP 909 809. These compounds, and metal complexes containing these compounds as ligands, are employed as what are called bleaching catalysts, together with a peroxygen compound, in detergents in order to lower the temperature at which the peroxygen compounds release the active oxygen. According to EP 909 809 the synthesis of these compounds proceeds in accordance with the following reaction scheme:

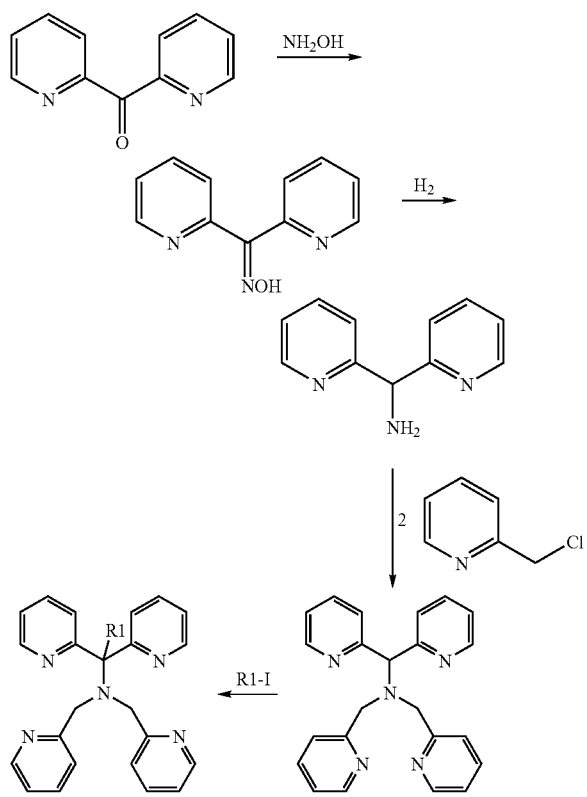

Starting from dipyridyl ketone, reaction with hydroxylamine forms the oxime, which is subsequently reduced to the amine.

The synthesis in the first reaction step takes place either with hydroxylamine in pyridine or with hydroxylamine hydrochloride in ethanol/water with addition of sodium hydroxide solution. Isolation is accomplished by neutralization and precipitation. In the second reaction step the product of the first reaction step is reduced to the amine using zinc and ammonia in ethanol. The yields, however, fluctuate greatly. In the third reaction step the primary amine is alkylated with picolyl chloride hydrochloride in 5N sodium hydroxide solution; the reaction time amounts to 40 h; the product is isolated as the perchlorate by precipitation with perchloric acid, and this perchlorate is washed and, where appropriate, recrystallized; the amine is liberated from the purified salt by reaction with sodium hydroxide solution, and is isolated by extraction with dichloromethane, drying of the organic phase, and concentration to dryness. In the fourth reaction step, freshly liberated amine in dry tetrahydrofuran is deprotonated with n-butyllithium and alkylated with methyl iodide; the mixture is warmed overnight to −30-0° C., and then Glauber's salt is added. Isolation is accomplished by concentration, takeup of the residue in dichloromethane, washing, drying, and further concentration; the crude product is reprecipitated from ethyl acetate/hexane. For the preparation of the corresponding metal complex compounds, the ligand obtained from reaction stages 1 to 4 and recrystallized is dissolved in methanol and reacted with a transition metal compound, such as iron(II) chloride tetrahydrate, for example, in solution in methanol. The solvent is stripped off completely under reduced pressure, and the hard, firmly adhering residue is recrystallized or extracted by stirring. The yields obtained for the ligands (stage 1 to 4) are in the range from 4.9% to 5.1%. The yields for the complexes (stage 1 to 5) are in the region of 3.5%.

The synthesis process described cannot be implemented on the industrial scale; the level of solvent use is high, the isolation of the products is problematic on safety grounds and cannot be implemented industrially in this way, the yields are poorly reproducible, and recycling of solvents is impossible.

The problem addressed was to develop a process for preparing the stated class of compound that is free from the drawbacks outlined above.

The invention provides a process for preparing N,N-bis(pyridin-2-ylmethyl)-1,1-bis(pyridin-2-yl)-1-aminoalkane compounds of formula 1

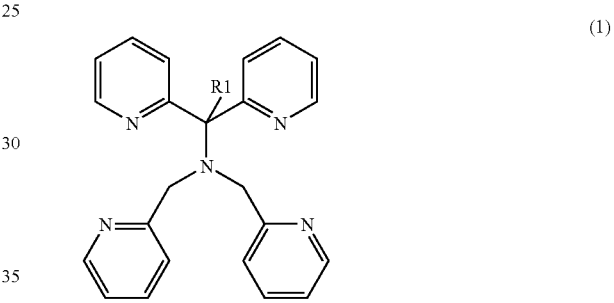

where $R^1$ is $C_1$-$C_6$ alkyl, phenyl or benzyl, preferably methyl. This process comprises 1) reacting dipyridyl ketone with hydroxylamine and reducing the resulting oxime, without isolating it, to the amine of the formula 2

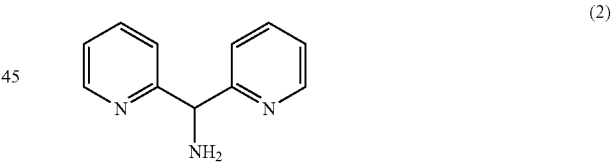

2) alkylating the amine of formula 2 first with 1 to 1.5 mole equivalents of picolyl chloride and then with a further 1 to 1.5 mole equivalents of picolyl chloride, to give the amine of the formula 3

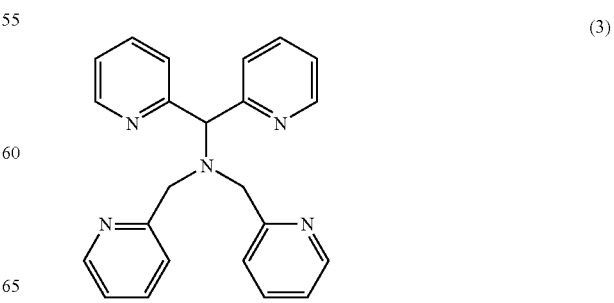

3) converting the resulting amine of formula 3 into the fluoroborate salt by addition of $HBF_4$, and then liberating the amine of formula 3 from this fluoroborate salt by addition of a base, and
4) alkylating the amine of formula 3 with an alkyl halide of the formula $R^1$-hal.

The process of the invention is carried out in detail as follows.

Reaction Step 1:

Dipyridyl ketone is introduced as an initial charge in methanol. With stirring, aqueous hydroxylamine solution is added at a rate such that the mixture increases in temperature but does not boil. The amount of hydroxylamine is about 1.0-1.2, preferably 1.05-1.15 mole equivalents. The mixture is heated to boiling and stirred at that temperature until reaction is complete. The reaction time amounts to 5 to 15 h, preferably 5 to 8 h. The mixture is subsequently cooled to room temperature. When this temperature has been reached, palladium on carbon is added as a catalyst. The amount of catalyst is about 1% to 5% by weight, based on the ketone employed. Then hydrogen is introduced with vigorous stirring at 15 to 50° C., preferably at 40 to 50° C., until the reduction is complete. After the end of the reaction, the clear, reddish solution is separated from the catalyst by filtration. For the isolation of the product, the solvent is distilled off completely under reduced pressure.

According to the process of the invention the intermediate of the formula 2 is obtained in yields >85%, preferably in yields of 88 to 91%, and in high purity (>90% purity by NMR).

Reaction Step 2:

The product of the first stage is admixed at room temperature with 5N sodium hydroxide solution. With cooling, a pre-prepared solution of picolyl chloride hydrochloride in water is added at a rate such that there is only a slight increase in the internal temperature. The amount of sodium hydroxide solution is 1.5-2.5, preferably 2.0-2.2 mole equivalents; the amount of picolyl chloride is 1.0-1.5, preferably 1.1-1.2 mole equivalents. Stirring is subsequently carried out at room temperature. The reaction time amounts to about 1 to 8 h, preferably 2-5 h. Then, in the same way, sodium hydroxide solution and picolyl chloride hydrochloride solution are added again in succession. The amount of sodium hydroxide solution is 1.5-2.5, preferably 2.0-2.2 mole equivalents; the amount of picolyl chloride is 1.0-1.5, preferably 1.1-1.2 mole equivalents. The mixture is subsequently stirred vigorously at room temperature for a number of days. The reaction time amounts to about 2-4, preferably 3 days. For isolation the reaction mixture is extracted with dichloromethane. Concentration gives the crude product as a viscous oil. Purification is accomplished by precipitation with HBF4 solution (50% strength in water) and simultaneous addition of saturated sodium chloride solution with cooling. The precipitate is isolated by filtration, washed, and dried.

This produces a fluoroborate salt that contains approximately 60% of the compound of the formula 3.

The amine can be liberated again from the salt as follows:

The salt is suspended finely in dichloromethane at room temperature. Then 5N sodium hydroxide solution is added and the mixture is stirred vigorously. The amount of sodium hydroxide solution is 5-10, preferably 6-7 mole equivalents, based on the primary amine employed. The reaction time amounts to 0.5 to 2 h, preferably 0.5 to 1 h. The product is worked up by separating the phases, extracting the aqueous phase with dichloromethane, drying the combined organic phases thoroughly over $Na_2SO_4$, and removing the solvent by distillation.

The product of the formula 3 is obtained according to this process of the invention in yields >50%, preferably in yields of 55% to 65%, and in high purity (>90% by HPLC).

Reaction Step 3:

Freshly liberated amine of the formula 3 is dissolved in THF and the solution is brought under argon to −60 to −80° C., preferably −75 to −65° C. At this temperature, cooled n-BuLi is added dropwise at a rate such that the temperature does not rise too sharply. The amount of n-BuLi is 1.0-1.2, preferably 1.05-1.15 mole equivalents. The internal temperature ought not to exceed −50° C., preferably not −65° C. After the end of the addition the mixture is stirred for some time. The reaction time amounts to 30-90, preferably 30-60 minutes. When this time has elapsed, TMEDA (N,N,N,N-tetramethylethylenediamine) is metered in at a rate such that the internal temperature does not rise more than 5 to 10° C., and stirring is carried out subsequently for a few minutes. The amount of TMEDA is 1.0-1.2, preferably 1.05-1.15 mole equivalents. In accordance with an analogous process, the alkyl iodide is then added. The amount of alkyl iodide is 1.0-1.5, preferably 1.1-1.2 mole equivalents. Subsequently the mixture is warmed with stirring first at 40 to −20, preferably −30° C., and then to −5 to +5° C. The reaction time amounts to 5-10, preferably 7 to 9 h. Subsequently, at 0° C., Glauber's salt is added and the composition is stirred for 15-60, preferably 3045 minutes. The amount of Glauber's salt is 0.1-0.2, preferably 0.15-0.17 mole equivalents.

The precipitate formed is isolated by filtration and washed with cold THF. If necessary it can be dried under reduced pressure.

The moist crude product is stirred vigorously in a 2-phase mixture of dichloromethane and 5N sodium hydroxide solution. The reaction time amounts to 5 to 15, preferably 8 to 10 h. Subsequently the phases are separated, the aqueous phase is extracted with dichloromethane, and the combined organic phases are dried thoroughly with sodium sulfate and concentrated to completion.

According to this process of the invention the product of the formula 1 is obtained in yields >60%, preferably in yields of 65% to 70%, and in high purity (about 95% by NMR/HPLC).

The process as described in EP 909 809 is unrealizable industrially in many respects: the amount of catalyst required is too large, the solvent mixtures used are difficult, if not indeed impossible, to separate, the mass of organic solvents used is extremely high, and the perchlorate precipitation is impossible on safety grounds.

Preparation in accordance with the process of the invention, in contrast, takes one fewer separate reaction step, and requires only four different organic solvents rather than seven. The mass of organic solvent used has been reduced to approximately 10%. The amount of expensive catalyst has likewise been reduced to 10%. The process can be carried out industrially, in comparison to the prior art.

The compounds of the formula 1 thus prepared can be used directly as bleach activators. Alternatively these compounds of the formula can be converted, by reaction with metal salts, into metal complex salts which contain the compounds of the formula 1 as ligands. A possible procedure for accomplishing this is, in detail, as follows:

A compound of the formula 1 is introduced as an initial charge in suspension in methanol. At room temperature, solid metal salt is added and the mixture is stirred. Suitable metal salts in this respect are Fe, Mn, Cr, and Co salts, preferably Fe salts.

The metal complex salts thus obtained are likewise suitable as bleaching catalysts. The reaction time amounts to 2 to 5, preferably, 3 to 4 h. Subsequently a portion of the solvent is distilled off under reduced pressure. The amount of solvent remaining is 10-20, preferably 10-15% of the amount employed. The product suspension obtained is admixed with ethyl acetate and extracted by stirring vigorously. The duration of extractive stirring is 1 to 5, preferably 2 to 3 h. Then the precipitate is isolated by filtration, washed with further ethyl acetate, and dried under reduced pressure.

According to this process of the invention the product is obtained in yields >90%, preferably in yields of 92% to 94%, and in high purity (about 94% by HPLC).

Examples below are intended to illustrate the invention without restricting it to them.

Stage 1:

1.37 l of methanol (1085 g) were introduced as an initial charge and 200 g (1.09 mol) of dipyridyl ketone were introduced. Then, with stirring, 65.6 ml (73.5 g) of hydroxylamine solution (1.14 mol of hydroxylamine) were added at a rate such that the mixture increased in temperature but did not boil (a suspension may form, but at a higher temperature a clear solution forms). The mixture was heated to reflux and stirred at that temperature until the reactant had been fully consumed by reaction (TLC monitoring; about 6 h). The mixture was cooled to room temperature and 2 g of palladium on carbon (1% by weight, based on ketone employed) were added. Then, at 50° C. and with vigorous stirring, hydrogen was introduced. After the end of reaction (TLC monitoring, about 4 h) the clear, reddish solution was separated from the catalyst by filtration. The product was isolated by distilling off the solvent under reduced pressure in a rotary evaporator.

This gave 193 g of 1,1-di(2-pyridyl)methylamine (91%) in the form of a red-brown oil.

Stage 2:

390.0 g of dipyridylmethylamine (95% pure, 2 mol) were admixed at room temperature with 1168 g (4.2 mol) of 5N sodium hydroxide solution. With cooling, a pre-prepared solution of 360.8 g (2.2 mol) of picolyl chloride hydrochloride in 700 ml of water was added at a rate such that the internal temperature did not exceed 35° C. Stirring was continued for 3 h and then in the same way, in succession, a further 1168 g (4.2 mol) of 5N sodium hydroxide solution and, again, a solution of 360.8 g (2.2 mol) of picolyl chloride hydrochloride in 700 ml of water were added. The reaction mixture was subsequently stirred vigorously at room temperature for 3 days. For isolation of the product, the reaction mixture was extracted with three times 1 L of dichloromethane. The organic extract was concentrated to completion on a rotary evaporator, giving 780 g of viscous crude product. For purification, 1406 g of HBF4 solution (50% strength in water) and 1018 ml of saturated sodium chloride solution were added with cooling. The composition was subsequently stirred for 1 h at room temperature and the precipitated crystals were then isolated by filtration, washed, and dried.

This gave 987 g of fluoroborate salt.

The salt was finely suspended in dichloromethane at room temperature.

Then 7.9 l of 5N sodium hydroxide solution were added, and the mixture was stirred vigorously for 30 minutes.

For working up, the phases were separated and the aqueous phase was extracted with twice 19.7 l of dichloromethane. The entire organic phases were dried thoroughly over Na2SO4, and the solvent was removed by distillation.

This gave 478 g of 1,1,1',1''-tetra(2-pyridyl)trimethylamine (65%) as a yellowish oil.

Stage 3:

511.8 g (1.39 mol) of freshly liberated 1,1,1',1''-tetra(2-pyridyl)trimethylamine were dissolved in THF and the solution was cooled to −70° C. under argon. The addition of 1000 ml (1.6 M in hexane=1.6 mol) of BuLi, cooled to 40° C. beforehand, took place at a rate such that the internal temperature did not rise above −65° C. The end of the addition was followed by stirring for a further 30 minutes. After this time had elapsed, 177.6 g (1.54 mol) of TMEDA (N,N,N,N-tetramethylethylenediamine) were metered in at a rate such that the internal temperature did not rise more than 5° C., and stirring was continued for 10 minutes. Then 226.5 g of methyl iodide (1.6 mol) were added in the same way. About 10 minutes after the end of the addition the reaction mixture had a temperature of −30° C. The mixture was stirred at this temperature for 6 h hours and then stirred at 0° C. until the next morning.

At this temperature, 49.8 g of Glauber's salt were added and stirring was continued for 30 minutes.

The precipitate formed was isolated by filtration on a glass frit, washed with twice 75 ml of cold THF, and dried under reduced pressure at 45° C.

The crude product obtained was suspended in 2.9 kg of dichloromethane. 8.5 l of 5N sodium hydroxide solution were added to this suspension, and the mixture was stirred vigorously. The phases were separated and the organic phase was washed with saturated NaCl solution, dried over Na2SO4, and concentrated to completion.

This gave 494.6 g (68%) of 1',1''-di(2-pyridyl)-1,1-di(2-pyridyl)dimethylethylamine as an off-white solid.

Stage 4: Preparation of an Iron(II) Chloride Complex with Ligand According to (I):

140 g (0.366 mol) of 1',1''-di(2-pyridyl)-1,1-di(2-pyridyl)dimethylamine were dissolved in 3 l of methanol. At room temperature 61.1 g (0.366 mol) of FeCl2×4H2O were added, followed by stirring for 3 h. After the end of the reaction time, 2.7 l of solvent (90%) were distilled off under reduced pressure. The product suspension obtained was then extracted by stirring with 3 l of ethyl acetate for about 2 h, and the precipitate was isolated by filtration and washed with a further 200 ml of ethyl acetate.

The moist product was dried under reduced pressure at 40° C.

This gave 171 g of product (92%) as a strongly red solid.

We claim:

1. A process for preparing a N,N-bis(pyridin-2-ylmethyl)-1,1-bis(pyridin-2-yl)-1-aminoalkane compound of formula 1, or a transition metal complex salt thereof as ligand,

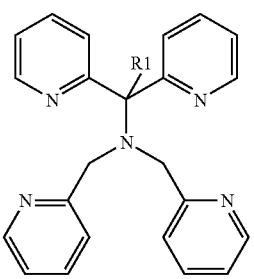

(1)

where R$^1$ is C$_1$-C$_6$ alkyl, phenyl or benzyl, said process comprising:

1) reacting dipyridyl ketone with hydroxylamine and reducing the resulting oxime, without isolating it, to provide an amine of formula 2

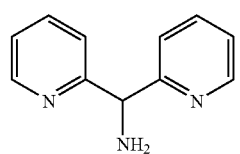

(2)

2) alkylating the amine of formula 2 first with 1 to 1.5 mole equivalents of picolyl chloride and then with a further 1 to 1.5 mole equivalents of picolyl chloride, to provide an amine of formula 3

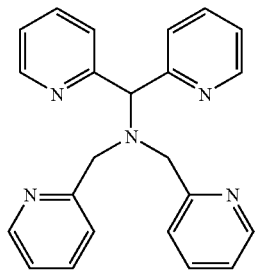

(3)

3) converting the amine of formula 3 into a fluoroborate salt by addition of $HBF_4$, and then liberating the amine of formula 3 from the fluoroborate salt by addition of a base, and 4) alkylating the amine of formula 3 with an alkyl halide of the formula $R^1$-hal to provide the compound of formula (1), and, optionally, 5) converting the compound of formula (1) into the transition metal complex salt, by further reacting the compound of formula (1) with a transition metal salt.

2. The process of claim 1, wherein $R^1$ is methyl.

3. The process of claim 1, wherein the compound of formula (1) is reacted with the transition metal salt to provide the transition metal complex salt of the compound of formula (1) as ligand.

* * * * *